(12) United States Patent
Noguchi et al.

(10) Patent No.: US 11,845,083 B2
(45) Date of Patent: Dec. 19, 2023

(54) CONTAINER

(71) Applicant: Enplas Corporation, Saitama (JP)

(72) Inventors: Koji Noguchi, Saitama (JP); Shigeru Uemura, Saitama (JP)

(73) Assignee: Enplas Corporation, Saitama (JP)

( * ) Notice: Subject to any disclaimer, the term of this patent is extended or adjusted under 35 U.S.C. 154(b) by 0 days.

(21) Appl. No.: 17/535,607

(22) Filed: Nov. 25, 2021

(65) Prior Publication Data

US 2022/0168729 A1    Jun. 2, 2022

(30) Foreign Application Priority Data

Nov. 30, 2020 (JP) ................................. 2020-198543

(51) Int. Cl.
  *B65D 39/00* (2006.01)
  *B65D 43/04* (2006.01)
  (Continued)

(52) U.S. Cl.
  CPC ..... *B01L 3/50825* (2013.01); *A61B 5/150351* (2013.01); *B01L 2300/042* (2013.01);
  (Continued)

(58) Field of Classification Search
  CPC .............. A61B 5/150351; A61J 1/1425; B01L 2300/042; B01L 2300/0832; B01L 2300/123; B01L 2200/0689; B01L 3/50825; B65D 39/04; B65D 39/0023; B65D 47/121; B65D 59/02; B65D 39/00; B65D 2539/003; B65D 2539/005; B65D 2539/001; F16L 55/11; F16L 55/1141; Y10S 215/03; Y10S 220/19

USPC ........ 220/200, 800, 801, 287, 789, DIG. 19; 215/294, 296, DIG. 1, DIG. 3, 355, 358, 215/361, 43; 138/89, 90; 422/550, 568, 422/916, 569; 277/612, 615
  See application file for complete search history.

(56) References Cited

U.S. PATENT DOCUMENTS

| 39,208 A | * | 7/1863 | Baxter | ................... | B65D 39/04 |
| | | | | | 215/270 |
| 368,228 A | * | 8/1887 | Morehouse | ............ | B65D 39/16 |
| | | | | | 215/364 |

(Continued)

FOREIGN PATENT DOCUMENTS

| AU | 2003262234 | 3/2004 |
| JP | 2004-077418 | 3/2004 |

*Primary Examiner* — Gideon R Weinerth (57) ABSTRACT

A container includes a container main body including a housing part and an opening, and a lid configured to close the opening and including an insertion part configured to be inserted to the opening. The outer peripheral surface of the insertion part includes first and second protrusions and first and second recesses. The inner peripheral surface of the opening includes third and fourth protrusions and third and fourth recesses. When the insertion part is temporarily inserted to the opening, the third protrusion presses the first recess in a state where the first protrusion is housed in the third recess. When the insertion part is fully inserted to the opening, the third protrusion presses the second recess and the fourth protrusion presses the first recess in a state where the first protrusion is housed in the fourth recess and the second protrusion is housed in the third recess.

20 Claims, 8 Drawing Sheets

(51) Int. Cl.
  *B65D 43/02*  (2006.01)
  *A61J 1/00*  (2023.01)
  *B01L 3/00*  (2006.01)
  *B65D 59/02*  (2006.01)
  *A61B 5/15*  (2006.01)

(52) U.S. Cl.
  CPC ....... *B01L 2300/0832* (2013.01); *B65D 39/00* (2013.01); *B65D 59/02* (2013.01); *B65D 2539/003* (2013.01)

(56) References Cited

U.S. PATENT DOCUMENTS

| | | | | |
|---|---|---|---|---|
| 487,451 A * | 12/1892 | Schroeder | ............. | B65D 39/00 215/355 |
| 487,452 A * | 12/1892 | Schroeder | ............. | B65D 39/00 215/355 |
| 588,784 A * | 8/1897 | Steffens | ................. | B65D 55/02 215/250 |
| 650,615 A * | 5/1900 | Salomon | ............ | B65D 51/1688 251/210 |
| 729,835 A * | 6/1903 | Barnes | .................. | B65D 39/16 251/319 |
| 2,196,785 A * | 4/1940 | Takiguchi | ............ | B65D 39/007 220/DIG. 19 |
| 2,370,535 A * | 2/1945 | Harrison | ............. | B65D 1/0246 215/355 |
| 2,746,632 A * | 5/1956 | Bramming | ............ | B65D 39/04 215/358 |
| 2,848,130 A * | 8/1958 | Jesnig | ................. | B65D 51/002 215/358 |
| 2,872,060 A * | 2/1959 | Brune | ................. | B65D 39/04 215/364 |
| 2,876,775 A * | 3/1959 | Barr, Sr. | .......... | A61B 5/150351 600/577 |
| 2,914,207 A * | 11/1959 | Moore | .................. | B65D 39/12 215/45 |
| 2,921,708 A * | 1/1960 | Marcel | .............. | B65D 39/0029 215/230 |
| 2,950,835 A * | 8/1960 | Alvear | ................ | B65D 47/121 215/358 |
| 3,017,050 A * | 1/1962 | Barr, Sr. | ............. | B01L 3/50825 D24/224 |
| 3,405,832 A * | 10/1968 | Lukesch | ................ | B65D 39/16 D9/439 |
| 3,578,027 A * | 5/1971 | Zopfi | ................... | F16L 55/1141 277/648 |
| 3,595,421 A * | 7/1971 | Sanchis | ................. | B65D 47/06 222/479 |
| 3,596,694 A * | 8/1971 | Jaeniche | ............... | B65D 39/04 215/45 |
| 3,661,291 A * | 5/1972 | Hetzer | ............... | F16L 55/1108 411/908 |
| 3,898,046 A * | 8/1975 | Ikeda | ................. | B01L 3/50825 422/550 |
| 3,900,122 A * | 8/1975 | Dichter | .................. | B65D 39/04 215/355 |
| 3,902,477 A * | 9/1975 | Gerarde | ........... | A61B 5/150343 600/573 |
| 4,057,160 A * | 11/1977 | Victor | ................ | B65D 41/0471 215/320 |
| 4,640,434 A * | 2/1987 | Johnsen | ................. | B64D 37/00 220/DIG. 19 |
| D289,796 S * | 5/1987 | Larkin | .......................... | D9/439 |
| 4,741,446 A * | 5/1988 | Miller | .................. | B01L 3/50825 215/247 |
| 4,871,077 A * | 10/1989 | Ogden | ............... | B65D 39/0076 220/254.1 |
| 4,883,641 A * | 11/1989 | Wicks | ........................ | A61L 2/28 435/31 |
| 5,167,923 A * | 12/1992 | Van Iperen | ................ | A61L 2/28 435/31 |
| 5,224,515 A * | 7/1993 | Foster | .................... | F16L 55/115 138/96 T |
| 5,246,434 A * | 9/1993 | Ebara | ................. | A61B 5/15003 600/573 |
| 5,327,942 A * | 7/1994 | Black | .................. | F16L 55/1141 138/92 |
| 5,711,446 A * | 1/1998 | Jeffs | ........................ | B65D 81/18 220/23.83 |
| 6,036,541 A * | 3/2000 | Koumatsu | ............. | H01R 13/443 439/275 |
| 7,934,614 B2 * | 5/2011 | Finneran | .............. | A61J 1/1425 215/363 |
| 8,833,398 B2 * | 9/2014 | Williams | ................. | F16L 55/11 215/296 |
| 8,910,818 B2 * | 12/2014 | Heiml | ................ | B65D 39/0052 215/296 |
| 9,340,338 B1 * | 5/2016 | Doherty | .............. | F16L 55/1141 |
| 9,700,163 B2 * | 7/2017 | Kobayashi | ......... | B65D 51/1622 |
| D971,118 S * | 11/2022 | Pelini | ..................... | B65D 39/04 D12/317 |
| 2002/0023893 A1* | 2/2002 | Sudo | .................... | B01L 3/50825 215/355 |
| 2004/0115096 A1* | 6/2004 | Itoh | ..................... | B01L 3/50825 422/400 |
| 2007/0284330 A1* | 12/2007 | Finneran | .............. | B65D 51/002 215/247 |
| 2008/0066820 A1* | 3/2008 | Williams | ............ | F16L 55/1141 138/91 |
| 2011/0084045 A1* | 4/2011 | Self | .................... | B65D 39/0017 215/364 |
| 2011/0108511 A1* | 5/2011 | McKinney | ......... | B65D 39/0017 215/355 |
| 2012/0192980 A1* | 8/2012 | Williams | ................. | F16L 55/11 29/428 |
| 2014/0175100 A1* | 6/2014 | Foresman | ........... | F16L 55/1612 220/305 |
| 2017/0030504 A1* | 2/2017 | Robillard | ............ | F16L 55/1141 |
| 2019/0015830 A1* | 1/2019 | Blaszcak | ............ | B01L 3/50825 |
| 2022/0016622 A1* | 1/2022 | Hunt | .................... | B01L 3/50825 |
| 2022/0168729 A1* | 6/2022 | Noguchi | ............ | B01L 3/50825 |

\* cited by examiner

CONTAINER

CROSS REFERENCE TO RELATED APPLICATIONS

This application is entitled to and claims the benefit of Japanese Patent Application No. 2020-198543, filed on Nov. 30, 2020, the disclosure of which including the specification, drawings and abstract is incorporated herein by reference in its entirety.

TECHNICAL FIELD

The present invention relates to a container for sealing.

BACKGROUND ART

In medical fields and the like, in some situation, test, analysis and the like are conducted by providing a sample such as blood and saliva to a container in which reagent is housed in advance and mixing them.

For example, PTL 1 discloses a measurement cell for a colorimeter or the like in which reagent is housed in advance. The opening of the measurement cell is sealed with a rubber cap. A sample is provided to the measurement cell after removing the cap from the opening of the measurement cell, and the material in the measurement cell is mixed by shaking the measurement cell after sealing the opening of the measurement cell with the cap, and thus, the test solution is adjusted in measurement cell. Then, a test, analysis and the like are conducted by measuring the light absorbance and the like of the test solution by using a colorimeter or the like, with the opening of the measurement cell sealed with the cap.

CITATION LIST

Patent Literature

PTL 1
Japanese Patent Application Laid-Open No. 2004-77418

SUMMARY OF INVENTION

Technical Problem

Preferably, a container that houses reagent in advance and is sealed with a cap for protecting the reagent from moisture and the like, as that disclosed in PTL 1, is configured such that the cap can be readily removed from the opening of the container in order to provide the sample into the container. However, the configuration in which the cap is readily removed from the opening of the container may increase the risk of the occurrence of a situation where the outside the container is contaminated due to the removal of the cap during the mixing of the sample or during the subsequent tests, analysis and the like.

An object of the present invention is to provide a container with a lid that can be removed for providing a sample, but is difficult to be removed after the sample is provided.

Solution to Problem

A container according to an embodiment of the present invention includes: a container main body including a housing part and an opening; and a lid including an insertion part configured to be inserted to the opening, the lid being configured to close the opening. An outer peripheral surface of the insertion part includes: a first protrusion disposed to surround a central axis of the insertion part, a second protrusion disposed to surround the central axis of the insertion part, on a base end side of the insertion part than the first protrusion, a first recess disposed between the first protrusion and the second protrusion to surround the central axis of the insertion part, and a second recess disposed to surround the central axis of the insertion part, on the base end side of the insertion part than the second protrusion. An inner peripheral surface of the opening includes: a third protrusion disposed to surround a central axis of the opening, a fourth protrusion disposed to surround the central axis of the opening, on a housing part side than the third protrusion, a third recess disposed between the third protrusion and the fourth protrusion to surround the central axis of the opening, and a fourth recess disposed to surround the central axis of the opening, on the housing part side than the fourth protrusion. When the insertion part is temporarily inserted to the opening, the third protrusion presses the first recess in a state where the first protrusion is housed in the third recess. When the insertion part is fully inserted to the opening, the third protrusion presses the second recess and the fourth protrusion presses the first recess in a state where the first protrusion is housed in the fourth recess and the second protrusion is housed in the third recess.

Advantageous Effects of Invention

According to the present invention, it is possible to provide a container with a lid that can be removed for providing a sample, but is difficult to be removed after the sample is provided.

DESCRIPTION OF EMBODIMENTS

Container 100 according to an embodiment of the present invention is described below. In container 100 according to the present embodiment, lid 110 is temporarily inserted before the sample is provided, and lid 110 is fully inserted after the sample is provided. In both the state where lid 110 is temporarily inserted and the state where lid 110 is fully inserted, the inside of container 100 is sealed by lid 110. The temporarily inserted lid 110 can be removed with some ease, but the fully inserted lid 110 is more difficult to remove than the temporarily inserted lid 110.

Configuration of Container

Figure 1:
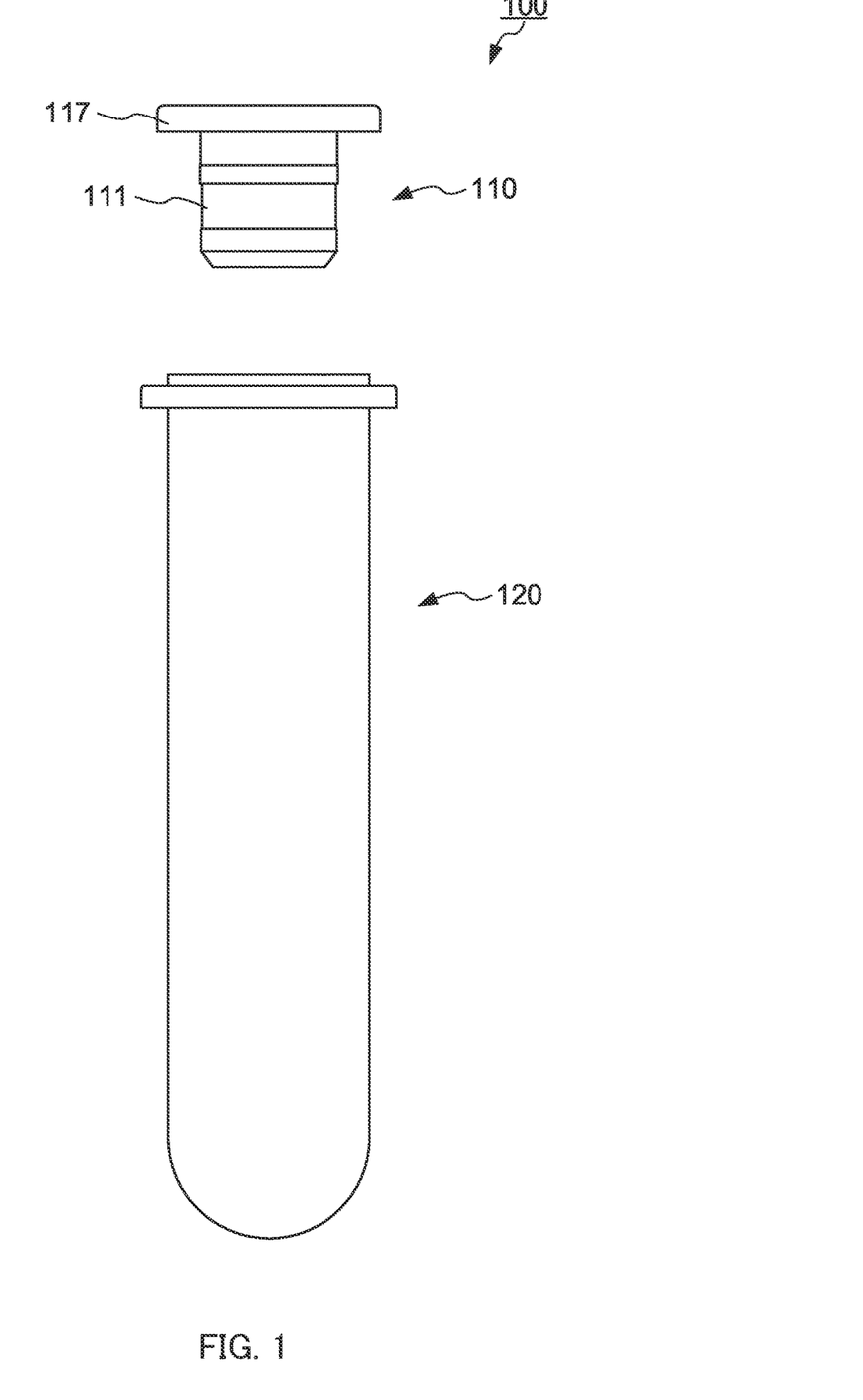
FIG. 1 is a front view of the container according to the embodiment.
Figure 2:
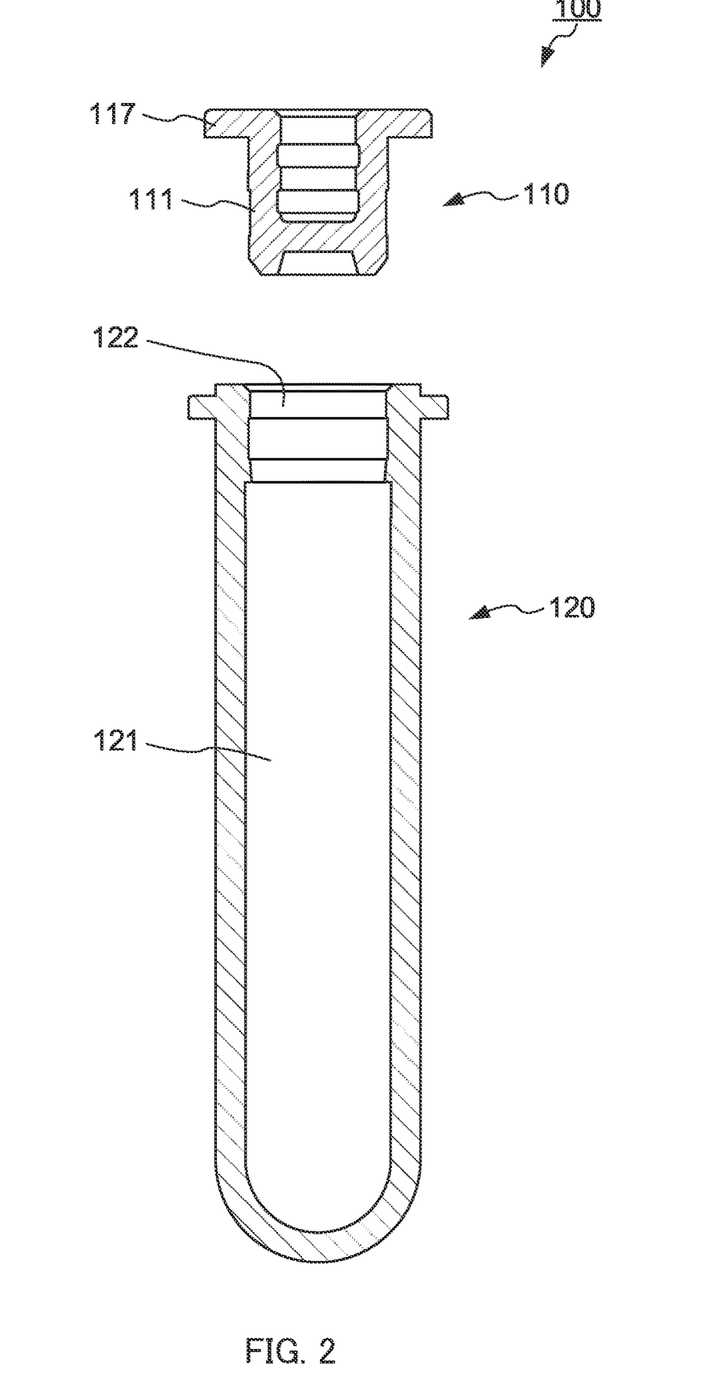
FIG. 2 is a sectional view of the container according to the embodiment.
Figure 3:
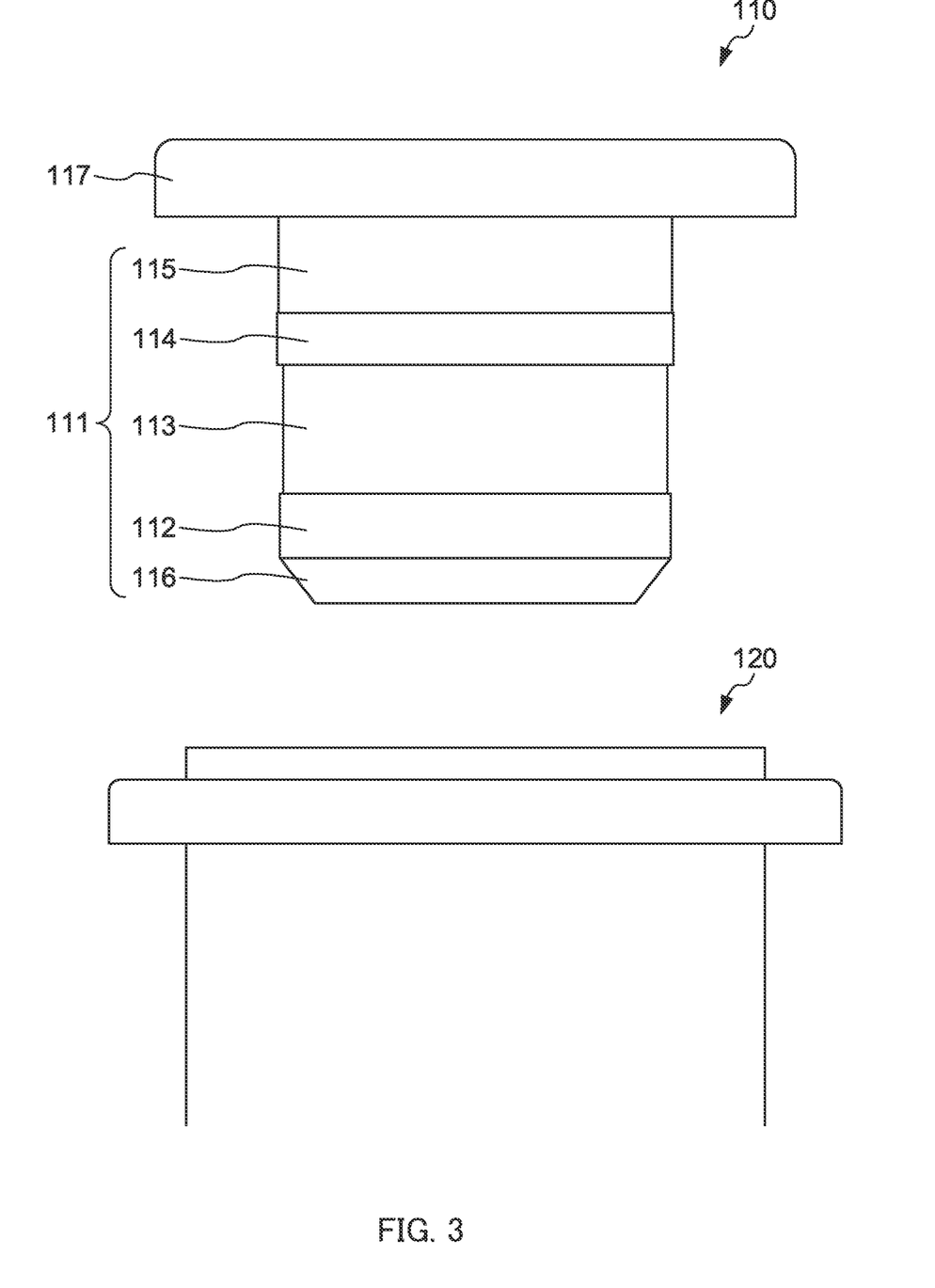
FIG. 3 is a partially enlarged front view of the container according to the embodiment.
Figure 4:
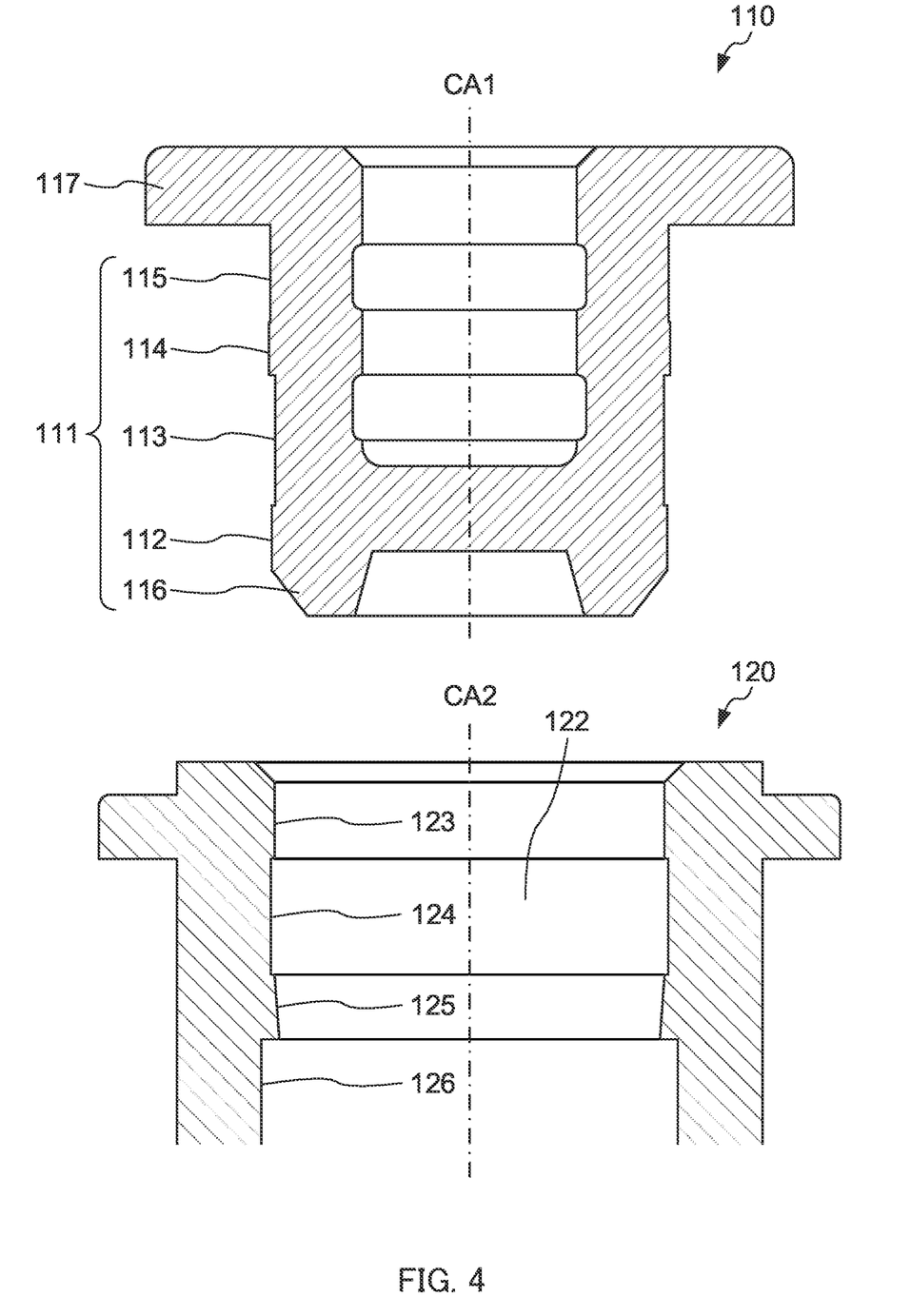
FIG. 4 is a partially enlarged sectional view of the container according to the embodiment.
Figure 5A:
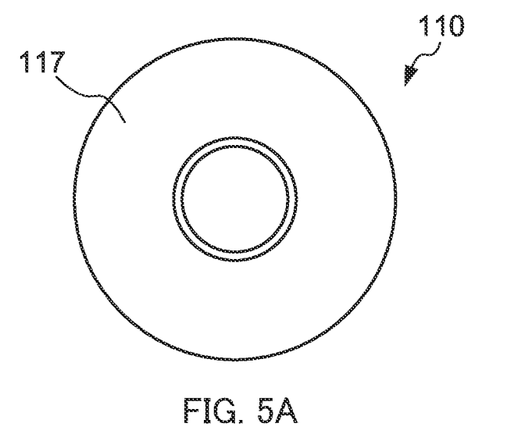
FIG. 5A a plan view of a lid.
Figure 5B:
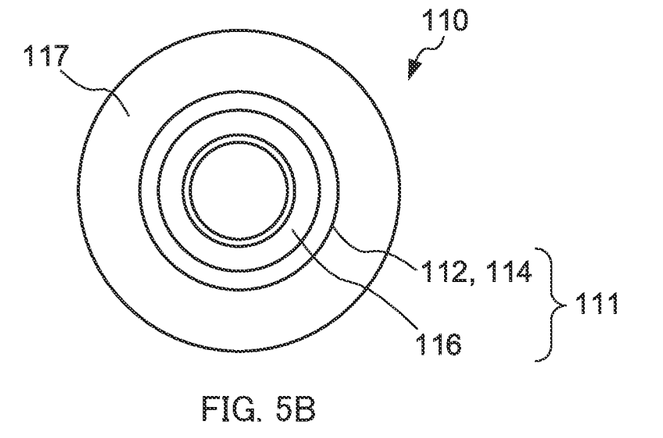
FIG. 5B is a bottom view of the lid.
Figure 5C:
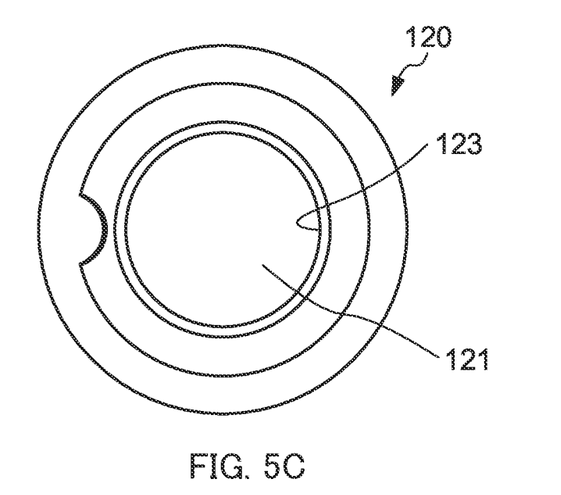
FIG. 5C is a plan view of a container main body.

FIG. 1 is a front view of container 100 according to the embodiment of the present invention. FIG. 2 is a sectional view of container 100. These drawings illustrate container 100 from which lid 110 is removed. FIG. 3 is a partially enlarged front view of container 100 illustrating a state of lid 110 and opening 122 of container main body 120. FIG. 4 is a partially enlarged sectional view of container 100 illustrating a state of lid 110 and opening 122 of container main body 120. FIG. 5A is a plan view of lid 110, FIG. 5B is a bottom view of lid 110, and FIG. 5C is a plan view of container main body 120.

As illustrated in FIGS. 1 and 2, container 100 includes lid 110 and container main body 120. Lid 110 includes insertion part 111. Container main body 120 includes housing part 121 and opening 122. Insertion part 111 of lid 110 is inserted to opening 122 of container main body 120, so as to seal housing part 121.

Lid 110 includes insertion part 111 that is inserted to opening 122 of container main body 120, and closes opening 122. In the present embodiment, lid 110 further includes flange part 117.

Insertion part 111 is a part that is inserted to opening 122 so as to close opening 122. The shape and size of insertion part 111 is appropriately set in accordance with opening 122. For example, in the case where opening 122 has a circular horizontal cross sectional shape, it is preferable that insertion part 111 also have a circular horizontal cross sectional shape of substantially the same size. In addition, in the case where opening 122 has a rectangular horizontal cross sectional shape, it is preferable that insertion part 111 also have a rectangular horizontal cross sectional shape of substantially the same size. In the present embodiment, the shape of insertion part 111 is a substantially columnar shape. In addition, it is preferable to provide a space inside insertion part 111. That is, it is preferable that insertion part 111 have a hollow structure. When insertion part 111 has a hollow structure, it is easy to deform insertion part 111, to insert insertion part 111 to opening 122, and to engage the protrusion of insertion part 111 and the protrusion of opening 122.

Flange part 117 is a part fixed to the base end portion of insertion part 111 and configured to be grabbed by the user, for example. The shape of flange part 117 is not limited and is appropriately selected in accordance with the purpose. In the present embodiment, flange part 117 is a plate-shaped member extending outward in a direction perpendicular to the central axis of insertion part 111. Flange part 117 may be formed integrally with insertion part 111, or may be formed as a member separated from insertion part 111 and fixed to insertion part 111. In the present embodiment, flange part 117 is formed integrally with insertion part 111.

The material of insertion part 111 is not limited as long as it has some elasticity. Examples of the material of insertion part 111 include elastomer, thermoplasticity polyurethane (TPU), silicone resin, and rubber. The material of flange part 117 is not limited, and may or may not be identical to the material of insertion part 111. In the present embodiment, the material of insertion part 111 and flange part 117 is elastomer. Lid 110 is manufactured by injection molding, for example.

As illustrated in FIGS. 3 and 4, the outer peripheral surface of insertion part 111 includes first protrusion 112, first recess 113, second protrusion 114 and second recess 115. In the present embodiment, insertion part 111 also includes top end part 116.

First protrusion 112 is a ridge formed on the outer peripheral surface of insertion part 111 to surround central axis CA1 of insertion part 111. First protrusion 112 is disposed between top end part 116 disposed on the top end side (housing part 121 side) and first recess 113 disposed on base end side (flange part 117 side). The outer diameter of first protrusion 112 is greater than the outer diameter of first recess 113. Thus, there is a step between first protrusion 112 and first recess 113. This step can engage with the step between third protrusion 123 and third recess 124 of opening 122 of container main body 120 during the temporary insertion (see FIG. 7), and can engage with the step between fourth protrusion 125 and fourth recess 126 of opening 122 during the full insertion (see FIG. 8). That is, this step functions as a stopper that prevents the removal of insertion part 111 from opening 122 during the temporary insertion and the full insertion.

First recess 113 is a valley line formed in the outer peripheral surface of insertion part 111 to surround central axis CA1 of insertion part 111, on the base end side of insertion part 111 than first protrusion 11. First recess 113 is disposed between first protrusion 112 disposed on the top end side and second protrusion 114 disposed on base end side. The outer diameter of first recess 113 is smaller than the outer diameter of first protrusion 112 and the outer diameter of second protrusion 114. First recess 113 is pressed by third protrusion 123 during the temporary insertion (see FIG. 7), and pressed by fourth protrusion 125 during the full insertion (see FIG. 8).

Second protrusion 114 is a ridge formed on the outer peripheral surface of insertion part 111 to surround central axis CA1 of insertion part 111, on the base end side of insertion part 111 than first protrusion 11. Second protrusion 114 is disposed between first recess 113 disposed on the top end side and second recess 115 disposed on base end side. The outer diameter of second protrusion 114 is greater than the outer diameter of first recess 113 and the outer diameter of second recess 115. Thus, there is a step between second protrusion 114 and second recess 115. This step can engage with the step between third protrusion 123 and third recess 124 of opening 122 during the full insertion (see FIG. 8). That is, this step functions as a stopper that prevents the removal of insertion part 111 from opening 122 during the full insertion. From the viewpoint of making insertion part 111 less easily removed from opening 122 during the full insertion than during the temporary insertion, it is preferable that the outer diameter of second protrusion 114 be greater than the outer diameter of first protrusion 112.

Second recess 115 is a valley line formed in the outer peripheral surface of insertion part 111 to surround central axis CA1 of insertion part 111, on the base end side of insertion part 111 than second protrusion 114. Second recess 115 is disposed between second protrusion 114 disposed on the top end side and flange part 117. The outer diameter of second recess 115 is smaller than the outer diameter of second protrusion 114. Second recess 115 is pressed by third protrusion 123 during the full insertion (see FIG. 8). From the viewpoint of making insertion part 111 less easily removed from opening 122 during the full insertion than during the temporary insertion, it is preferable that the outer diameter of second recess 115 be greater than the outer diameter of first recess 113. In addition, the outer diameter of second recess 115 may be greater than the outer diameter of first protrusion 112.

Top end part 116 is a part disposed on the top end side of insertion part 111 than first protrusion 112. The shape of top end part 116 is not limited as long as the functions of first protrusion 112, first recess 113, second protrusion 114 and second recess 115 are not affected. In the present embodiment, in view of easily inserting insertion part 111 to opening 122, top end part 116 has a tapered shape whose outer diameter decreases toward the top end side.

Container main body 120 includes housing part 121 and opening 122, and houses reagents, samples or the like. Reagent or the like may be housed in advance in container main body 120.

Housing part 121 is a bottomed recess for housing reagents, samples or the like. The shape and size of housing part 121 are not limited, and may be appropriately set in accordance with the application and the like. While the inner space of housing part 121 is blocked from the outside by lid 110, a through hole, a channel and the like connected to the outside of housing part 121 may be formed in the wall that makes up housing part 121. When the inner space of housing part 121 should be blocked from the outside, such a through hole, channel and the like are closed with other members, for example.

Opening 122 is a part that connects between the outside and housing part 121 in container main body 120. The position of opening 122 is not limited, but preferably is an upper part in container main body 120 from the viewpoint of suppressing leakage of the sample inside housing part 1 to the outside. In the present embodiment, opening 122 is open upward at the topmost part of container main body 120.

The material of container main body 120 is not limited as long as the material has a desired strength, and may be appropriately selected in accordance with the application and manufacturing method. The examples of the material of container main body 120 include resin, glass and metal. In the present embodiment, the material of container main body 120 is polypropylene. Container main body 120 is manufactured by injection molding, for example.

As illustrated in FIG. 4, the inner peripheral surface of opening 122 includes third protrusion 123, third recess 124, fourth protrusion 125 and fourth recess 126.

Third protrusion 123 is a ridge formed on the inner peripheral surface of opening 122 to surround central axis CA2 of opening 122. Third protrusion 123 is disposed between the outside end portion (upper side end portion) of opening 122 and third recess 124 disposed on the housing part 121 side (lower side). The inner diameter of third protrusion 123 is smaller than the inner diameter of third recess 124. Thus, there is a step between third protrusion 123 and third recess 124. This step can engage with the step between first protrusion 112 and first recess 113 of insertion part 111 of lid 110 during the temporary insertion (see FIG. 7), and can engage with the step between second protrusion 114 and second recess 115 during the full insertion (see FIG. 8). That is, this step functions as a stopper that prevents the removal of insertion part 111 from opening 122 during the temporary insertion and the full insertion.

Third recess 124 is a valley line formed in the inner peripheral surface of opening 122 to surround central axis CA2 of opening 122, on housing part 121 side than third protrusion 123. Third recess 124 is disposed between third protrusion 123 disposed on the outer side and fourth protrusion 125 disposed on housing part 121 side. The inner diameter of third recess 124 is greater than the inner diameter of third protrusion 123 and the inner diameter of fourth protrusion 125. Third recess 124 houses first protrusion 112 of insertion part 111 so as not to cause large plastic deformation during the temporary insertion (see FIG. 7), and houses second protrusion 114 during the full insertion (see FIG. 8). That is, third recess 124 functions as a deformation suppression part for first protrusion 112 that prevents the large plastic deformation of first protrusion 112 during the temporary insertion.

Fourth protrusion 125 is a ridge formed on the inner peripheral surface of opening 122 to surround central axis CA2 of opening 122, on housing part 121 side than third protrusion 123. Fourth protrusion 125 is disposed between third recess 124 disposed on the outer side and fourth recess 126 disposed on housing part 121 side. The inner diameter of fourth protrusion 125 is smaller than the inner diameter of third recess 124 and the inner diameter of fourth recess 126. Thus, there is a step between fourth protrusion 125 and fourth recess 126. This step can engage with the step between first protrusion 112 and first recess 113 of insertion part 111 during the full insertion (see FIG. 8). That is, this step functions as a stopper that prevents the removal of insertion part 111 from opening 122 during the full insertion. From the viewpoint of making insertion part 111 less easily removed from opening 122 during the full insertion than during the temporary insertion, it is preferable that the inner diameter of fourth protrusion 125 be smaller than the inner diameter of third protrusion 123. Note that in FIG. 4, fourth protrusion 125 is illustrated as a tapered surface, but the inner surface of fourth protrusion 125 may be parallel to central axis CA2 of opening 122, or may be tilted such that the inner diameter decreases as it goes toward housing part 121.

Fourth recess 126 is a valley line formed in the outer peripheral surface of opening 122 to surround central axis CA2 of opening 122, on housing part 121 side than fourth protrusion 125. Fourth recess 126 is disposed between fourth protrusion 125 disposed on the outer side and housing part 121. The inner diameter of fourth recess 126 is greater than the inner diameter of fourth protrusion 125. Fourth recess 126 houses first protrusion 112 during the full insertion (see FIG. 8).

Figure 7:
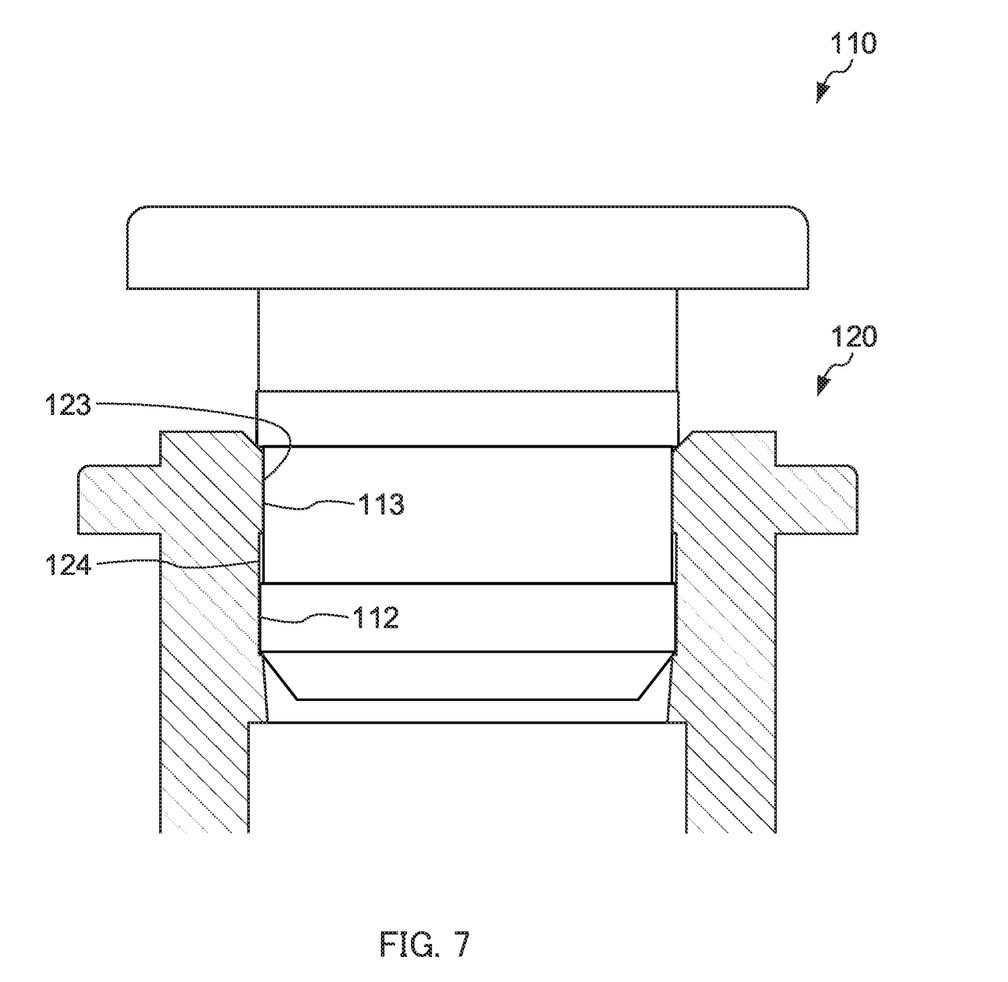
FIG. 7 is a diagram illustrating a state where the lid is temporarily inserted to the opening of the container main body.

As described above, when insertion part 111 of lid 110 is temporarily inserted to opening 122 of container main body 120, third protrusion 123 of opening 122 presses first recess 113 of insertion part 111, with first protrusion 112 of insertion part 111 housed in third recess 124 of opening 122 (see FIG. 7). In this manner, opening 122 is closed with insertion part 111, and housing part 121 is blocked from the outside. In addition, in this state, when pulled by the user with a first force, insertion part 111 can be removed from opening 122.

Figure 8:
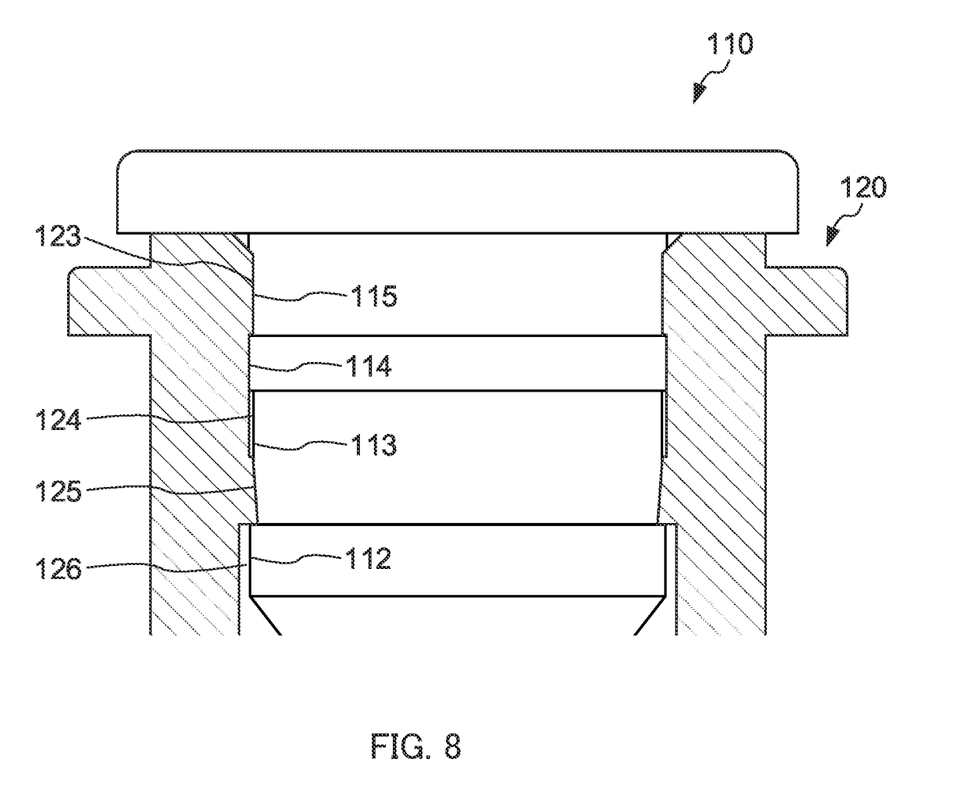
FIG. 8 is a diagram illustrating a state where the lid is fully inserted to the opening of the container main body.

On the other hand, when insertion part 111 is fully inserted to opening 122, third protrusion 123 and fourth protrusion 125 of opening 122 press second recess 115 and first recess 113, respectively, with first protrusion 112 and second protrusion 114 of insertion part 111 housed in fourth recess 126 and third recess 124 of opening 122, respectively (see FIG. 8). In this manner, opening 122 is closed with insertion part 111, and housing part 121 is blocked from the outside. In addition, in this state, even when pulled by the user with the first force, insertion part 111 cannot be removed from opening 122, and insertion part 111 cannot be removed from opening 122 unless it is pulled by the user with a second force a far larger than the first force.

To achieve the above-described functions of insertion part 111 and opening 122, it is preferable that third recess 124 of opening 122 be configured such that even after insertion part 111 is temporarily inserted to opening 122, first protrusion 112 of insertion part 111 engages with the step between fourth protrusion 125 and fourth recess 126 of opening 122 when insertion part 111 is fully inserted to opening 122. For example, if insertion part 111 is temporarily inserted to opening 122 over a long period of time in the case where the outer diameter of first protrusion 112 of insertion part 111 is significantly larger than the inner diameter of third recess 124 of opening 122, first protrusion 112 of insertion part 111 is plastically deformed by being largely deformed by third recess 124 of opening 122. If first protrusion 112 of insertion part 111 is plastically deformed in this manner, first protrusion 112 of insertion part 111 may not possibly be engaged with the step between fourth protrusion 125 and fourth recess 126 of opening 122 when insertion part 111 is fully inserted to opening 122. In view of this, in container 100 according to the present embodiment, the shape of third recess 124 of opening 122 is adjusted such that even when insertion part 111 is temporarily inserted to opening 122 over a long period of time, a large plastic deformation of first protrusion 112 of insertion part 111 to the extent that it cannot engage with the step between fourth protrusion 125 and fourth recess 126 of opening 122 is prevented. For example, it is preferable that the inner diameter of third recess 124 be equal to or greater than the outer diameter of first protrusion 112, and it is more preferable that the inner diameter of third recess 124 be greater than the outer diameter of first protrusion 112. In this manner, even when insertion part 111 is temporarily inserted to opening 122, first protrusion 112 of insertion part 111 is not substantially deformed by third recess 124 of opening 122. Thus, when insertion part 111 is fully inserted to opening 122, first protrusion 112 of insertion part 111 can reliably engage with the step between fourth protrusion 125 and fourth recess 126 of opening 122.

In addition, from the viewpoint of reliably closing opening 122 when insertion part 111 is temporarily inserted to opening 122, it is preferable that the inner diameter of third protrusion 123 of opening 122 be smaller than the outer diameter of first recess 113 of insertion part 111. Likewise, from the viewpoint of reliably closing opening 122 when insertion part 111 is fully inserted to opening 122, it is preferable that the inner diameter of third protrusion 123 of opening 122 be smaller than the outer diameter of second recess 115 of insertion part 111, and that the inner diameter of fourth protrusion 125 of opening 122 be smaller than the outer diameter of first recess 113 of insertion part 111.

In addition, from the viewpoint of preventing the removal of insertion part 111 from opening 122 when insertion part 111 is temporarily inserted to opening 122, it is preferable that the inner diameter of third protrusion 123 of opening 122 be smaller than the outer diameter of first protrusion 112 of insertion part 111. Likewise, from the viewpoint of preventing the removal of insertion part 111 from opening 122 when insertion part 111 is fully inserted to opening 122, it is preferable that the inner diameter of third protrusion 123 of opening 122 be smaller than the outer diameter of second protrusion 114 of insertion part 111, and that the inner diameter of fourth protrusion 125 of opening 122 be smaller than the outer diameter of first protrusion 112 of insertion part 111.

In addition, from the viewpoint of preventing further insertion of insertion part 111 into opening 122 when insertion part 111 is temporarily inserted to opening 122, it is preferable that the inner diameter of third protrusion 123 of opening 122 be smaller than the outer diameter of second protrusion 114 of insertion part 111.

Note that while a single product is composed only of container 100 in FIGS. 1 and 2, the container according to the embodiment of the present invention is not limited to this aspect. For example, the container according to the embodiment of the present invention may be a single container included in a set of a plurality of containers.

In addition, while lid 110 and container main body 120 are separated from each other in FIGS. 1 and 2, the container according to the embodiment of the present invention is not limited to this aspect. For example, lid 110 and container main body 120 may be connected together through a connecting member. In this case, one or both of lid 110 and container main body 120 may be integral with the connecting member.

Usage of Container

Figure 6:
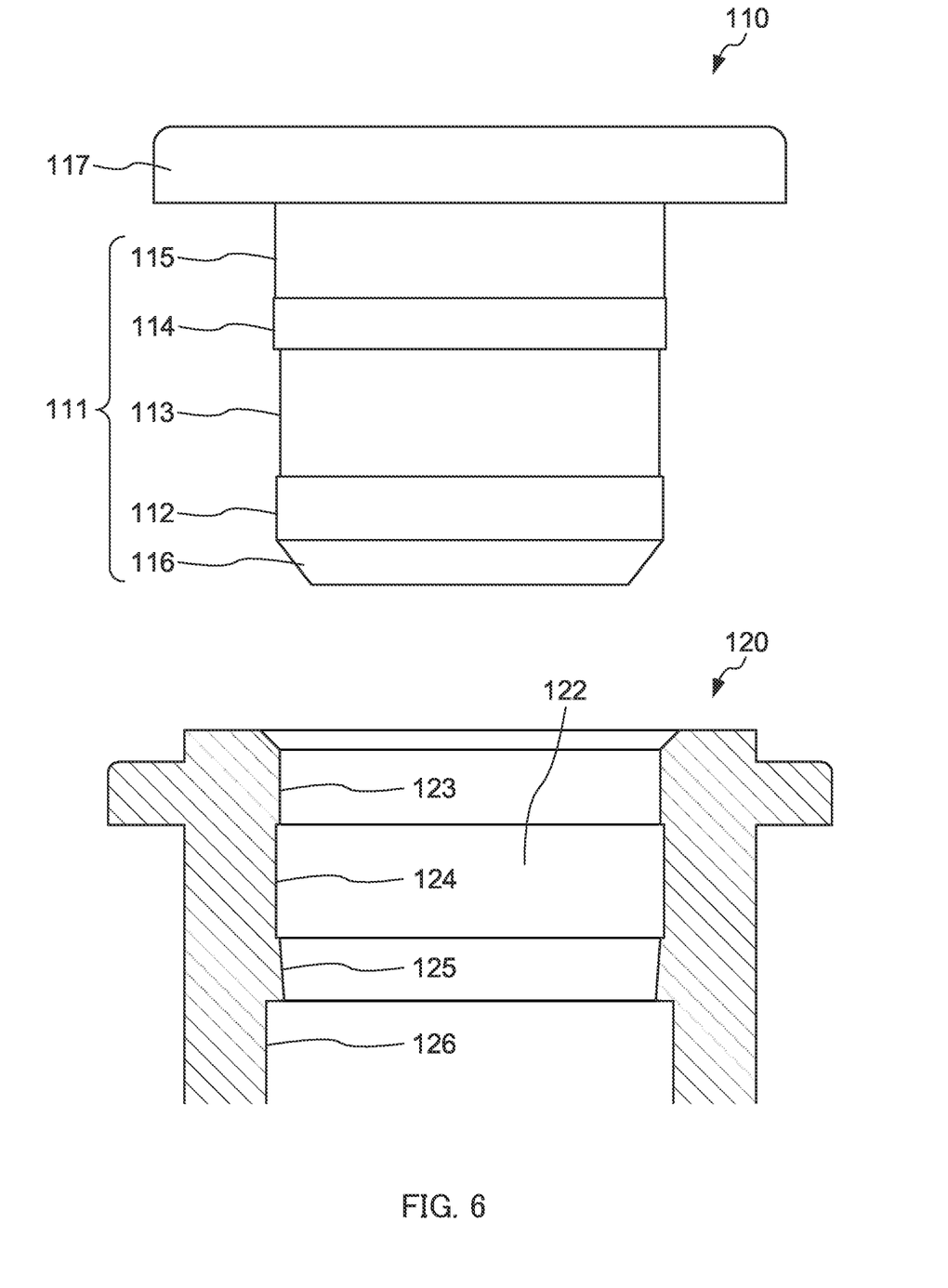
FIG. 6 is a diagram illustrating a state where the lid is not inserted to the opening of the container main body.

Next, an example of a usage of container 100 is described. FIGS. 6 to 8 are diagrams for describing a usage of container 100 and illustrate a state of lid 110 and opening 122 of container main body 120. FIG. 6 is a diagram illustrating a state where insertion part 111 of lid 110 is not inserted to opening 122. FIG. 7 is a diagram illustrating a state where insertion part 111 is temporarily inserted to opening 122. FIG. 8 is a diagram illustrating a state where insertion part 111 is fully inserted to opening 122. In these drawings, in order to easily distinguish lid 110 and container main body 120 from each other, lid 110 is illustrated in a front view while container main body 120 is illustrated in a sectional view.

As illustrated in FIG. 6, reagent or the like is housed in housing part 121 of container main body 120 in the state where insertion part 111 of lid 110 is removed from opening 122 of container main body 120. Then, as illustrated in FIG. 7, insertion part 111 of lid 110 is slightly inserted to opening 122 of container main body 120, for temporary insertion. In this state, first protrusion 112 of insertion part 111 is housed in third recess 124 of opening 122, while third protrusion 123 of opening 122 presses first recess 113 of insertion part 111. In this manner, opening 122 is closed with insertion part 111, and housing part 121 is blocked from the outside. Thus, the reagent or the like in housing part 121 is protected from moisture and the like. In addition, since first protrusion 112 of insertion part 111 is housed in third recess 124 of opening 122, first protrusion 112 of insertion part 111 is not largely plastically deformed even when the temporary insertion state is continued for a long time.

As illustrated in FIG. 7, in the state where insertion part 111 of lid 110 is temporarily inserted to opening 122 of container main body 120, only the step between first protrusion 112 and first recess 113 of insertion part 111 engages with the step between third protrusion 123 and third recess 124 of opening 122, and functions as a stopper that prevents the removal of insertion part 111 from opening 122. In this manner, only one step functions as a stopper, and therefore in this state, insertion part 111 can be removed from opening 122 when pulled by the user with the first force as illustrated in FIG. 6. For example, when conducting a test, analysis or the like using container 100, the user removes insertion part 111 of lid 110 from opening 122 of container main body 120, and provides a sample such as blood and saliva to housing part 121 of container main body 120.

Thereafter, as illustrated in FIG. 8, insertion part 111 of lid 110 is strongly inserted to opening 122 of container main body 120, for full insertion. In this state, first protrusion 112 and second protrusion 114 of insertion part 111 are housed in fourth recess 126 and third recess 124 of opening 122, respectively, while third protrusion 123 and fourth protrusion 125 of opening 122 press second recess 115 and first recess 113 of insertion part 111, respectively. In this manner, opening 122 is closed with insertion part 111, and housing part 121 is blocked from the outside.

In addition, in this state, the step between first protrusion 112 and first recess 113 of insertion part 111 engages with the step between fourth protrusion 125 and fourth recess 126 of opening 122 and functions as a stopper that prevents the removal of insertion part 111 from opening 122, while the step between second protrusion 114 and second recess 115 of insertion part 111 engages with the step between third protrusion 123 and third recess 124 of opening 122 and functions as a stopper that prevents the removal of insertion part 111 from opening 122. Further, at this time, under the influence of first recess 113 of insertion part 111 pressed by fourth protrusion 125 of opening 122, first protrusion 112 of insertion part 111 projects and deforms toward fourth recess 126 of opening 122 side. In this manner, since the two steps function as stoppers, insertion part 111 cannot be removed from opening 122 even when the user pulls it with the first force, and insertion part 111 cannot be removed from opening 122 unless it is pulled with the second force a far larger than the first force. Thus, after insertion part 111 of lid 110 is fully inserted to opening 122 of container main body 120, the sample does not leak to the outside of container 100 even when the sample and the reagent are agitated by strongly shaking container 100. In addition, even when container 100 is discarded after a test, analysis or the like afterward, the sample does not leak to the outside of container 100.

Effect

With container 100 according to the present embodiment, before the sample is provided, insertion part 111 of lid 110 can be temporarily inserted to opening 122 of container main body 120 such that it can be readily removed and that housing part 121 can be sealed, while after the sample is provided, insertion part 111 of lid 110 can be fully inserted to opening 122 of container main body 120 such that it is less easily removed than in the temporarily inserted state. Thus, with container 100 according to the present embodiment, the preliminarily housed reagent can be protected before the sample is provided, while the leakage of the sample to the outside can be prevented after the sample is provided.

INDUSTRIAL APPLICABILITY

The container according to the embodiment of the present embodiment is suitable for the test, analysis, and the like in the medical field, for example.

REFERENCE SIGNS LIST

100 Container
110 Lid
111 Insertion part
112 First protrusion
113 First recess
114 Second protrusion
115 Second recess
116 Top end part
117 Flange part
120 Container main body
121 Housing part
122 Opening
123 Third protrusion
124 Third recess
125 Fourth protrusion
126 Fourth recess
CA1 Central axis of insertion part
CA2 Central axis of opening

The invention claimed is:

1. A container comprising:
a container main body including a housing part and an opening; and
a lid including an insertion part configured to be inserted to the opening, the lid being configured to close the opening,
wherein an outer peripheral surface of the insertion part includes:
a first protrusion disposed to surround a central axis of the insertion part,
a second protrusion disposed to surround the central axis of the insertion part, at a position closer to a base end of the insertion part than the first protrusion,
a first recess disposed between the first protrusion and the second protrusion to surround the central axis of the insertion part, and
a second recess disposed to surround the central axis of the insertion part, at a position closer to the base end of the insertion part than the second protrusion,
wherein an inner peripheral surface of the opening includes:
a third protrusion disposed to surround a central axis of the opening,
a fourth protrusion disposed to surround the central axis of the opening, at a position closer to the housing part than the third protrusion,
a third recess disposed between the third protrusion and the fourth protrusion to surround the central axis of the opening, and
a fourth recess disposed to surround the central axis of the opening, at a position closer to the housing part than the fourth protrusion,
wherein an outer diameter of the second recess is greater than an outer diameter of the first recess,
wherein an inner diameter of the fourth protrusion is smaller than an inner diameter of the third protrusion,
wherein when the insertion part is temporarily inserted to the opening, the third protrusion presses the first recess in a state where the first protrusion is housed in the third recess, and
wherein when the insertion part is fully inserted to the opening, the third protrusion presses the second recess and the fourth protrusion presses the first recess in a state where the first protrusion is housed in the fourth recess and the second protrusion is housed in the third recess.

2. The container according to claim 1, wherein the third recess is configured such that the first protrusion engages with a step between the fourth protrusion and the fourth recess when the insertion part is fully inserted to the opening even after the insertion part is temporarily inserted to the opening.

3. The container according to claim 1,
wherein the inner diameter of the third protrusion is smaller than the outer diameter of the first recess, and smaller than the outer diameter of the second recess; and
wherein the inner diameter of the fourth protrusion is smaller than the outer diameter of the first recess.

4. The container according to claim 2,
wherein the inner diameter of the third protrusion is smaller than the outer diameter of the first recess, and smaller than the outer diameter of the second recess; and
wherein the inner diameter of the fourth protrusion is smaller than the outer diameter of the first recess.

5. The container according to claim 1, wherein an inner diameter of the third recess is equal to or greater than an outer diameter of the first protrusion.

6. The container according to claim 2, wherein an inner diameter of the third recess is equal to or greater than an outer diameter of the first protrusion.

7. The container according to claim 3, wherein an inner diameter of the third recess is equal to or greater than an outer diameter of the first protrusion.

8. The container according to claim 4, wherein an inner diameter of the third recess is equal to or greater than an outer diameter of the first protrusion.

9. The container according to claim 5, wherein the inner diameter of the third recess is greater than the outer diameter of the first protrusion.

10. The container according to claim 6, wherein the inner diameter of the third recess is greater than the outer diameter of the first protrusion.

11. The container according to claim 7, wherein the inner diameter of the third recess is greater than the outer diameter of the first protrusion.

12. The container according to claim 8, wherein the inner diameter of the third recess is greater than the outer diameter of the first protrusion.

13. The container according to claim 1, wherein the lid includes elastomer.

14. The container according to claim 2, wherein the lid includes elastomer.

15. The container according to claim 3, wherein the lid includes elastomer.

16. The container according to claim 4, wherein the lid includes elastomer.

17. The container according to claim 5, wherein the lid includes elastomer.

18. The container according to claim 6, wherein the lid includes elastomer.

19. The container according to claim 7, wherein the lid includes elastomer.

20. The container according to claim 8, wherein the lid includes elastomer.

\* \* \* \* \*